US012171540B2

(12) United States Patent
Jang

(10) Patent No.: US 12,171,540 B2
(45) Date of Patent: Dec. 24, 2024

(54) HEAD-DEDICATED MAGNETIC RESONANCE IMAGING DEVICE

(71) Applicant: MYBRAIN CO., LTD., Seongnam-si (KR)

(72) Inventor: Woo Ju Albert Jang, New York City, NY (US)

(73) Assignee: MYBRAIN CO., LTD., Seongnam-si (KR)

(*) Notice: Subject to any disclaimer, the term of this patent is extended or adjusted under 35 U.S.C. 154(b) by 151 days.

(21) Appl. No.: 17/927,110

(22) PCT Filed: May 24, 2021

(86) PCT No.: PCT/KR2021/006390
§ 371 (c)(1),
(2) Date: Nov. 22, 2022

(87) PCT Pub. No.: WO2021/246696
PCT Pub. Date: Dec. 9, 2021

(65) Prior Publication Data
US 2023/0200674 A1    Jun. 29, 2023

(30) Foreign Application Priority Data

May 26, 2020    (KR) .................. 10-2020-0062932

(51) Int. Cl.
*A61B 5/055*    (2006.01)
*A61B 5/00*    (2006.01)
(Continued)

(52) U.S. Cl.
CPC .............. *A61B 5/055* (2013.01); *A61B 5/004* (2013.01); *G01R 33/34007* (2013.01); *G01R 33/3802* (2013.01); *G01R 33/3854* (2013.01)

(58) Field of Classification Search
None
See application file for complete search history.

(56) References Cited

U.S. PATENT DOCUMENTS 5,617,856 A * 4/1997 Tamura .................. A61B 5/245
324/261
6,043,653 A * 3/2000 Takamori ........... G01R 33/3854
324/309
(Continued)

FOREIGN PATENT DOCUMENTS

JP      2018-110863 A    7/2018
KR    2012-0037724 A    4/2012
(Continued)

OTHER PUBLICATIONS

Ramirez et al., "head-only MRI system," (Jul. 24, 2020), <https://www.designboom.com/technology/researchers-develop-head-only-mri-system-Jul. 24, 2020/>). (Year: 2020).*

*Primary Examiner* — Joel Lamprecht
*Assistant Examiner* — Ashish S Jasani
(74) *Attorney, Agent, or Firm* — You & IP, LLC

(57) ABSTRACT

The present disclosure relates to a head-dedicated magnetic resonance imaging (MRI) device, wherein a head-dedicated image is acquired in a state in which a head of a subject is positioned in a center of a magnetic field of a main magnet installed in a housing, a local coil manufactured in in the form of being inserted into or worn in a human body of the subject is utilized to acquire an image of a selected portion to be examined (for example, an oral region, an ear region, and an eye region) of the head, or a vibration absorber installed around the housing absorbs vibrations caused by the Lorentz force generated by a magnetic field of the main magnet and a current applied to a gradient coil while the image is acquired in a state in which the housing is hung on an installation frame.

5 Claims, 7 Drawing Sheets

(51) Int. Cl.
*G01R 33/34* (2006.01)
*G01R 33/38* (2006.01)
*G01R 33/385* (2006.01)

(56) References Cited

U.S. PATENT DOCUMENTS

| | | | |
|---|---|---|---|
| 6,181,228 B1 * | 1/2001 | Laskaris | H01F 6/04 |
| | | | 505/894 |
| 2008/0039712 A1 * | 2/2008 | Graves | A61B 5/055 |
| | | | 600/411 |
| 2012/0146645 A1 | 6/2012 | Rasche et al. | |
| 2012/0288820 A1 * | 11/2012 | Choe | A61B 5/4542 |
| | | | 433/29 |
| 2013/0190608 A1 * | 7/2013 | Schmidt | G01R 33/3873 |
| | | | 600/422 |
| 2015/0369888 A1 | 12/2015 | Calvert | |
| 2018/0199853 A1 | 7/2018 | Abkai et al. | |

FOREIGN PATENT DOCUMENTS

| | | | | |
|---|---|---|---|---|
| KR | 20120037724 | * | 4/2012 | A61B 5/055 |
| KR | 2012-0049236 A | | 5/2012 | |
| KR | 20130136022 A | * | 12/2013 | A61B 5/055 |
| WO | 2006-062028 A1 | | 6/2006 | |
| WO | 2014-001014 A1 | | 1/2014 | |

* cited by examiner

HEAD-DEDICATED MAGNETIC RESONANCE IMAGING DEVICE

BACKGROUND

1. Field of the Invention

The present disclosure relates to a magnetic resonance imaging (MRI) device, and more particularly, to a head-dedicated MRI device.

2. Discussion of Related Art

Magnetic resonance imaging (MRI) devices are medical diagnostic imaging devices that use radio frequency (RF) electromagnetic waves and magnetic fields, which are non-ionizing radiation, to obtain images showing an internal cross section of a human body without radiation exposure.

The MRI device generates magnetic resonance by applying the RF electromagnetic waves to hydrogen nucleuses among various substances that constitute the human body positioned in the magnetic field and acquires, as an image, a magnetic resonance signal received at relaxation at which the hydrogen nucleuses emit, to the surroundings, energy obtained due to a magnetic resonance phenomenon after the RF electromagnetic waves are blocked.

An MRI device according to the related art (KR 10-1152537 B1) includes a main magnet that is installed in a housing produced in a hollow cylindrical body and applies a magnetic field to the human body moving into the hollow of the housing, a gradient coil that is installed in the housing and applies a gradient magnetic field that temporarily changes a magnetic field intensity of the main magnet according to the position of a portion to be examined (for example, an axial position formed by the X axis, the Y-axis, and the Z-axis or linear combinations of these axes) to encode information on the position of the portion to be examined of the human body, and an RF coil that is installed in the housing, applies the RF electromagnetic waves that causes the magnetic resonance phenomenon in the human body, blocks the RF electromagnetic waves, and then receives the magnetic resonance signal.

Since the MRI device according to the related art is used for the whole body and acquires an image by moving a subject lying on a movable cradle to a center of the magnetic field of the main magnet in a large housing, the device is disadvantageous to a subject with claustrophobia and is large and expensive.

Meanwhile, in the MRI device according to the related art, which is used for the whole body, since movement of the subject is restricted in a closed space inside the housing, in particular, when a functional MRI (fMRI) image obtained by measuring brain activity by detecting changes related to blood flow is acquired, a function of a brain that can be seen through the corresponding fMRI is limited.

SUMMARY OF THE INVENTION

The present disclosure is directed to providing a head-dedicated magnetic resonance imaging (MRI) device in which a main magnet, a gradient coil, and a radio frequency (RF) coil are installed inside a housing manufactured in a hollow cylindrical shape and which acquires a head-dedicated image in a state in which the head of the subject is positioned in a center of a magnetic field of the main magnet installed inside the housing or acquires an image of a selected portion to be examined (for example, an oral region, an ear region, and an eye region) of the head using a local coil manufactured to be inserted into or worn on the body of the subject, and absorbs, using a vibration absorber installed around the housing, vibrations caused by the Lorentz force generated by a magnetic field of the main magnet and a current applied to the gradient coil while acquiring an image in the housing is hung on an installation frame.

A head-dedicated magnetic resonance imaging (MRI) device includes a main magnet is manufactured in a hollow cylindrical body such that only a head and a portion of a shoulder of a subject are accommodated in an inner hollow and applies electromagnetic waves to the head of the subject, positioned in the inner hollow, a gradient coil that is manufactured in a hollow cylindrical body installed in close contact with an inner diameter part of the main magnet and applies a gradient magnetic field that temporarily changes a magnetic field intensity of the main magnet according to the position of a portion to be examined, to encode information on the position of a portion to be examined of the head of the subject located in the inner hollow, a radio frequency (RF) coil that is manufactured in a hollow cylindrical body installed in close contact with the inner diameter part of the gradient coil, applies RF electromagnetic waves causing a magnetic resonance phenomenon inside the head of the subject positioned in the inner hollow, blocks the RF electromagnetic waves, and then receives a magnetic resonance signal for acquiring an image of the entire head of the subject, a local coil that is manufactured in the form of being inserted into or worn in a human body of the subject, and after the RF coil applies the RF electromagnetic waves causing the magnetic resonance phenomenon into the head of the subject, and blocks the RF electromagnetic waves, receives the magnetic resonance signal for acquiring an image of a selected portion to be examined of the head of the subject, a control device that controls a pulse sequence applied to the gradient coil and the RF coil to determine application or blocking timing of the gradient magnetic field or application or blocking timing of the RF electromagnetic waves to be required for acquiring an image of the entire head of the subject or the selected portion to be examined among the head of the subject, acquires an image of the entire head for brain diagnosis from the magnetic resonance signal received by the RF coil, and acquires an image of the selected portion to be examined (for example, an oral region, an ear region, and an eye region) among the head from the magnetic resonance signal received by the local coil, a housing which is manufactured in a hollow cylindrical shape such that only the head and the portion of the shoulder of the subject are accommodated in the inner hollow and in which the main magnet, the gradient coil, and the RF coil are installed, an installation frame that includes a ceiling portion and a wall portion to which the housing is fixed, and a vibration absorber that is interposed between an upper surface portion of the housing and the ceiling portion of the installation frame, between a side wall portion of the housing and the wall portion of the installation frame, or between a bottom surface of the housing and a floor in which the installation frame is installed, connects the housing and the installation frame, and absorbs vibrations caused by the Lorentz force generated by the magnetic field of the main magnet and a current applied to the gradient coil while an image is acquired.

The main magnet, the gradient coil, and the RF coil may be installed in the housing in a vertically upright state such that only the head and the portion of the shoulder of the subject are accommodated in the inner hollow.

The control device may stop a function of receiving the magnetic resonance signal by the local coil while the RF coil receives the magnetic resonance signal and stops a function of receiving the magnetic resonance signal by the RF coil while the local coil receives the magnetic resonance signal.

The local coil may be any one of a mouthpiece-type oral coil inserted into a mouth to acquire an image for dental diagnosis of the subject, a headphone-type ear coil fixed to a portion around an ear to acquire an image for otologic diagnosis of the subject, and an eyeglass-type eye coil fixed to a portion around an eye to acquire an image for ophthalmic diagnosis of the subject.

The vibration absorber may absorb vibrations caused by the Lorentz force generated by the magnetic field of the main magnet and the current applied to the gradient coil while an image is acquired in a state in which the housing is hung on the installation frame.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
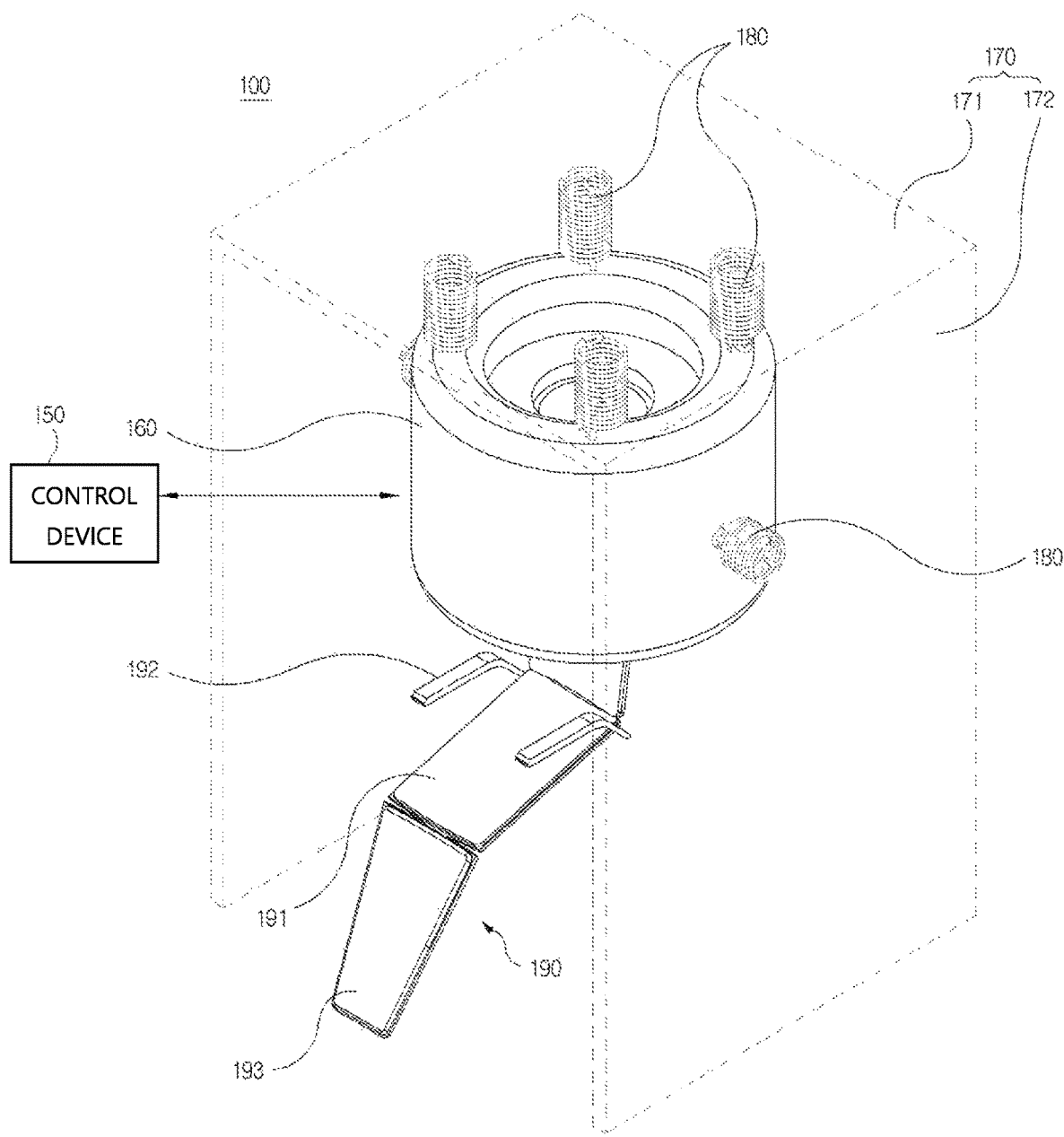
FIG. 1 is a perspective view illustrating a component of a head-dedicated magnetic resonance imaging (MRI) device according to the present disclosure.
Figure 2:
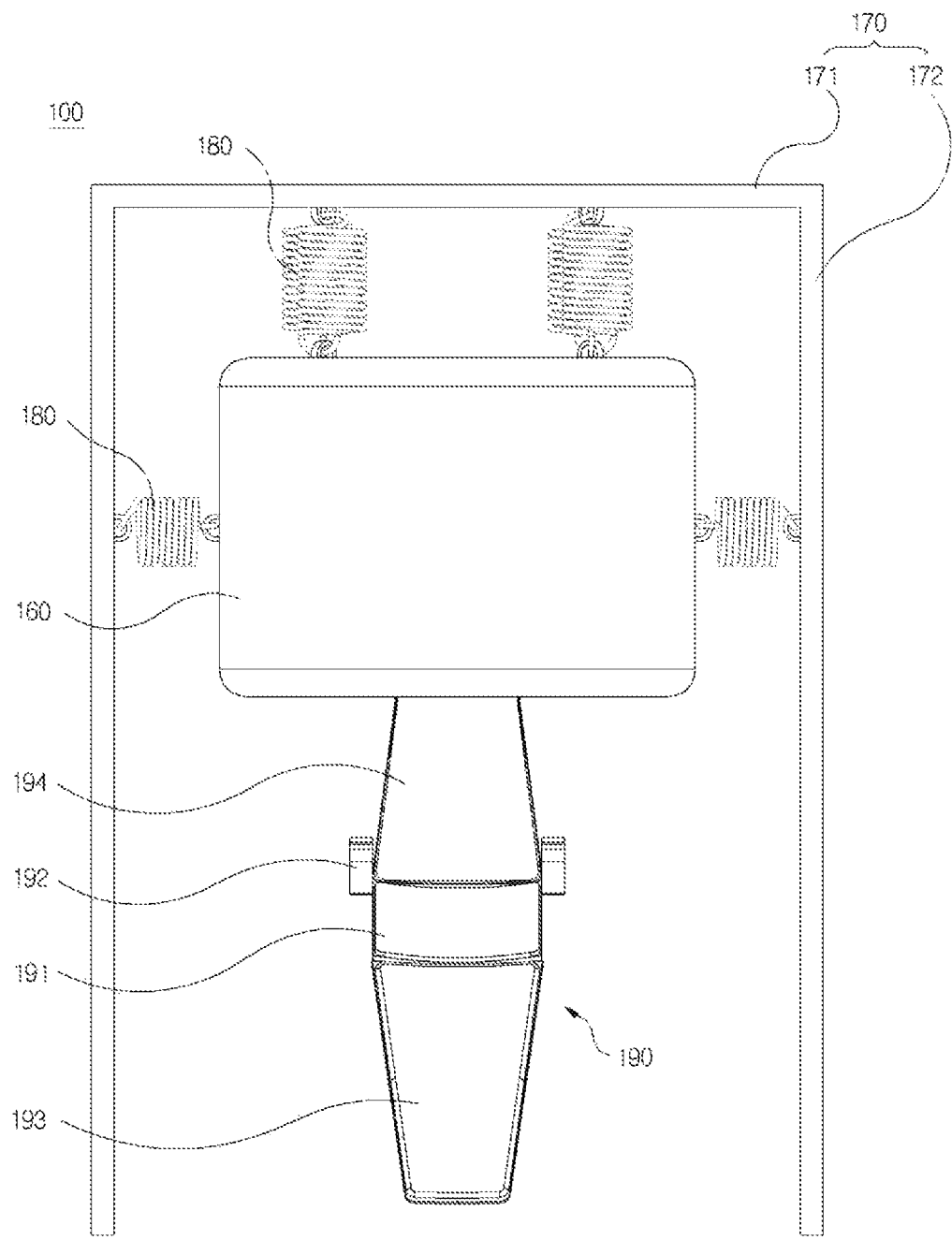
FIG. 2 is a front view of FIG. 1.
Figure 3:
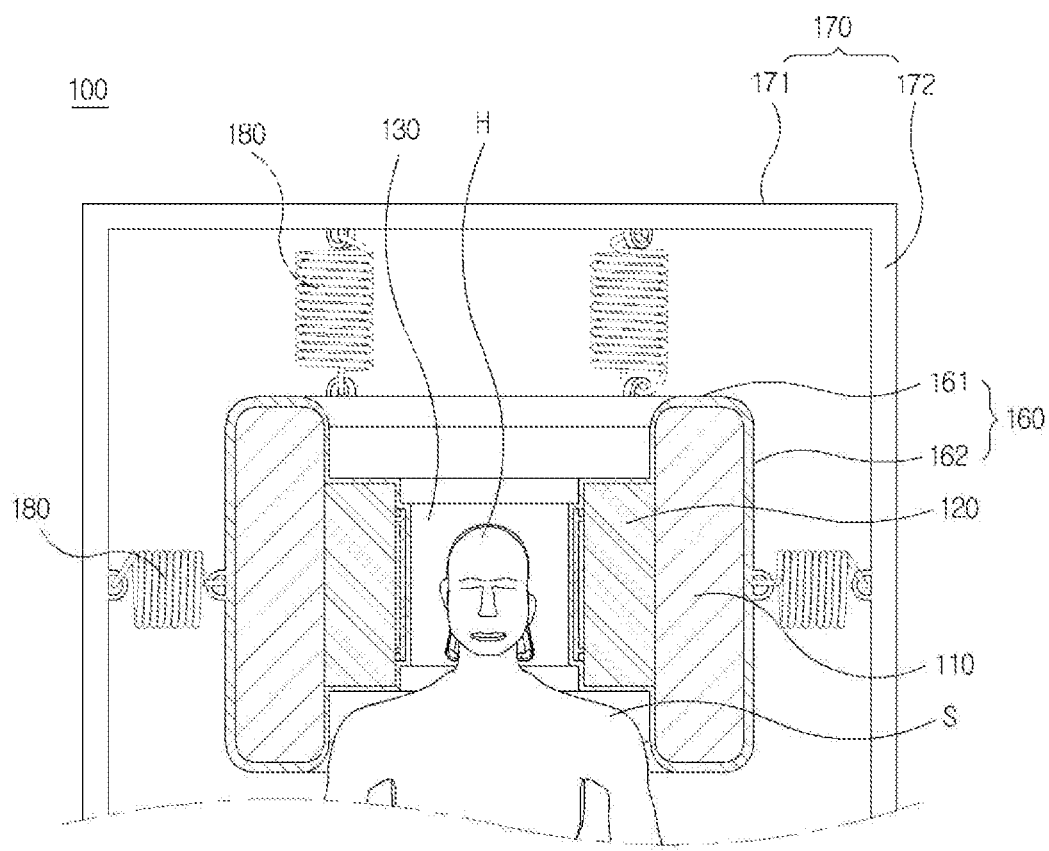
FIG. 3 is a front cross-sectional view of FIG. 1.
Figure 4:
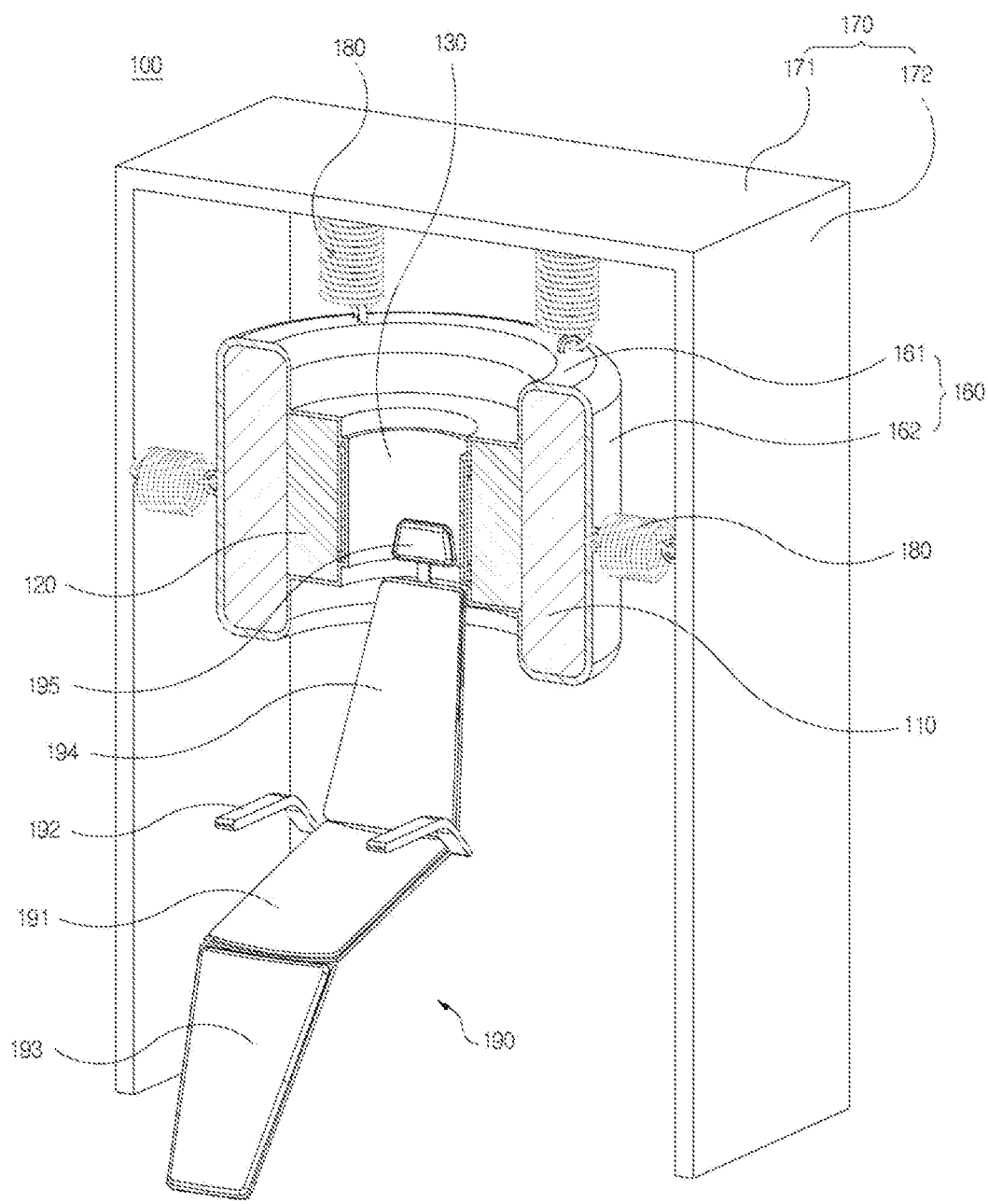
FIG. 4 is a cross-sectional perspective view of FIG. 1.

Hereinafter, embodiments of the present disclosure will be described in more detail with reference to the accompanying drawings.

A head-dedicated magnetic resonance imaging (MRI) device according to the present disclosure, which will be described below, is not limited to the following embodiments, and the technical spirit belongs to modifications that may be derived by those skilled in the art to which the corresponding technical field pertains without departing from the subject matter of the technology claimed in the appended claims.

Referring to FIGS. 1 to 7, a head-dedicated MRI device 100 according to the present disclosure includes a main magnet 110, a gradient coil 120, a radio frequency (RF) coil 130, a local coil 140, a control device 150, a housing 160, an installation frame 170, a vibration absorber 180, and a subject chair 190.

The main magnet 110 is manufactured in a hollow cylindrical body such that only a portion of a head H and a portion of a shoulder S of a subject are accommodated in an inner hollow and applies a magnetic field to the head H of the subject positioned in the inner hollow.

It is preferable that the main magnet 110 be manufactured such that an inner diameter of the inner hollow is large enough to sufficiently accommodate the entire head H and a portion of the shoulder S of the subject to satisfy the homogeneity of the magnetic field applied to the head H of the subject.

The gradient coil 120 is manufactured in a hollow cylindrical body installed in close contact with an inner diameter part of the main magnet 110 and applies a gradient magnetic field that temporarily changes a magnetic field intensity of the main magnet 110 according to the position of a portion to be examined, to encode information on the position of the portion to be examined of the head H of the subject located in the inner hollow.

It is preferable that the gradient coil 120 is manufactured such that the inner diameter of the inner hollow is large enough to accommodate the entire head H of the subject.

The RF coil 130 is manufactured in a hollow cylindrical body installed in close contact with the inner diameter part of the gradient coil 120, applies RF electromagnetic waves causing a magnetic resonance phenomenon inside the head H of the subject positioned in the inner hollow, blocks the RF electromagnetic waves, and then receives a magnetic resonance signal for acquiring an image of the entire head H of the subject.

It is preferable that the RF coil 130 be manufactured such that the inner diameter of the inner hollow is large enough to accommodate the entire head H of the subject.

In the embodiment of the present disclosure, as illustrated in FIGS. 1 to 7, it is preferable that the main magnet 110, the gradient coil 120, and the RF coil 130 be installed in the housing 160 in a vertically upright state such that only the head H and the portion of the shoulder S of the subject are accommodated in the inner hollow.

The local coil 140 is manufactured in the form of being inserted into or worn in a human body of the subject, and after the RF coil 130 applies the RF electromagnetic waves causing the magnetic resonance phenomenon into the head H of the subject, and blocks the RF electromagnetic waves, receives the magnetic resonance signal for acquiring an image of a selected portion to be examined (for example, an oral region, an ear region, and an eye region) of the head H of the subject.

Figure 5:
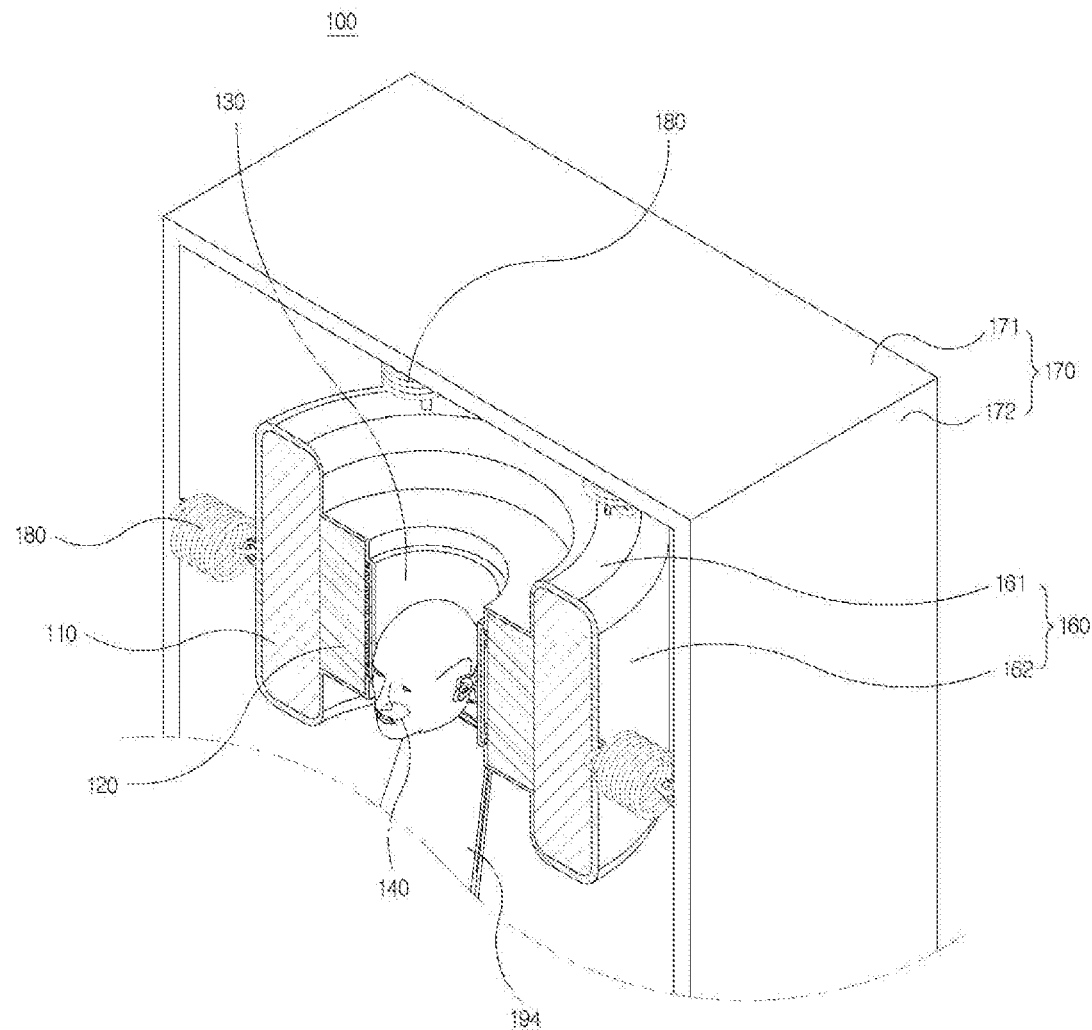
FIG. 5 is a view illustrating an in-use state of an oral coil.

As illustrated in FIG. 5, the local coil 140 may be manufactured and used as a mouthpiece-type oral coil inserted into a mouth to obtain an image for dental diagnosis of the subject.

Figure 6:
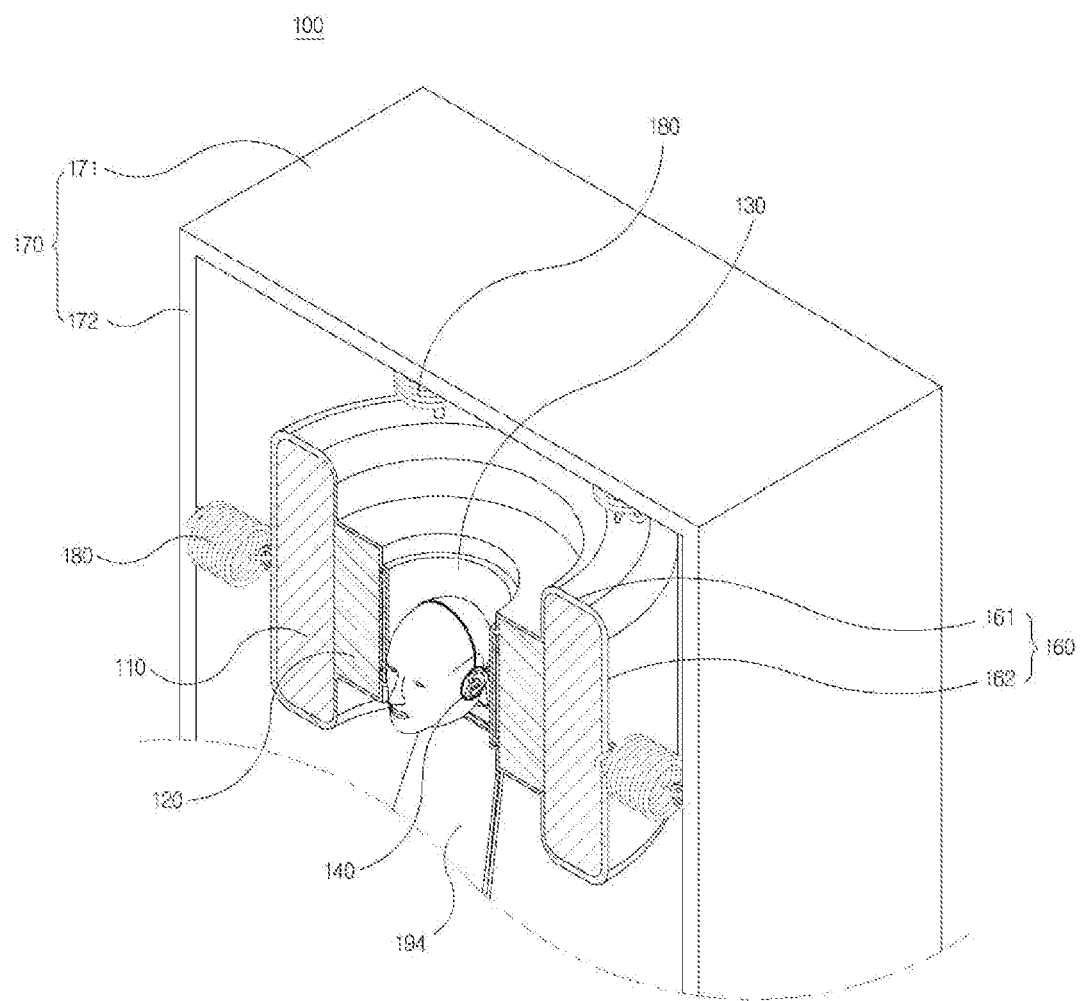
FIG. 6 is a view illustrating an in-use state of an ear coil.

As illustrated in FIG. 6, the local coil 140 may be manufactured and used as a headphone-type ear coil fixed to a portion around an ear to obtain an image for otologic diagnosis of the subject.

Figure 7:
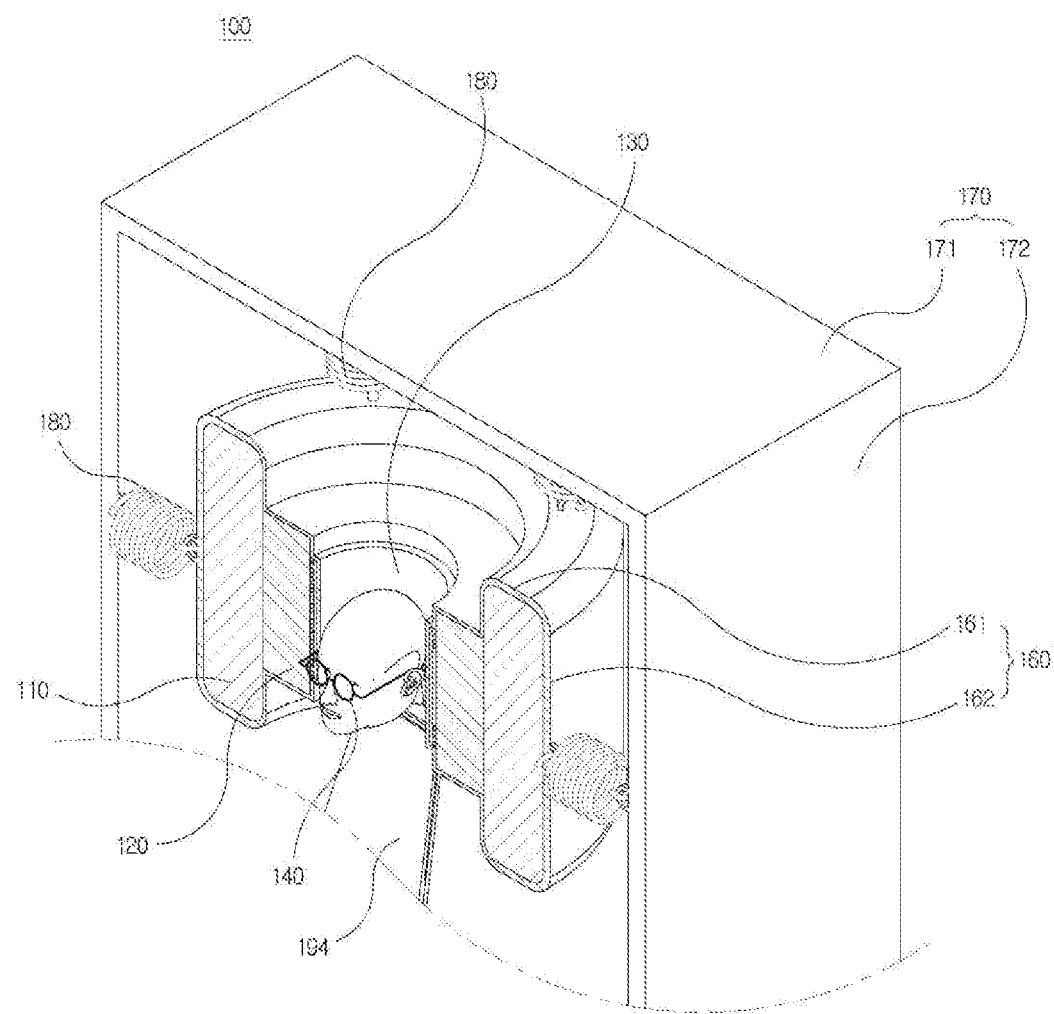
FIG. 7 is a view illustrating an in-use state of an eye coil.

As illustrated in FIG. 7, the local coil 140 may be manufactured and used as an eyeglass-type ear coil fixed to a portion around an eye to obtain an image for ophthalmic diagnosis of the subject.

For reference, as illustrated in FIGS. 5 to 7, in the head-dedicated MRI device 100 according to the present disclosure, since the local coil 140 manufactured in the form of being inserted into or worn in the human body of the subject is utilized, an image of the selected portion (for example, an oral region, an ear region, and an eye region) of the head H may be acquired with a high signal-to-noise ratio. For example, the local coil 140 may receive the magnetic resonance signal at a position close to the portion to be examined as compared to the RF coil 130, and thus acquire the image of the corresponding portion to be examined with a high signal-to-noise ratio.

The control device 150 controls a pulse sequence applied to the gradient coil 120 and the RF coil 130 to determine application or blocking timing of the gradient magnetic field or application or blocking timing of the RF electromagnetic waves to be required for acquiring an image of the entire head of the subject or the selected portion to be examined (for example, an oral region, an ear region, and an eye region) among the head of the subject or.

The control device 150 acquires an image of the entire head for brain diagnosis from the magnetic resonance signal received by the RF coil 130 and acquires an image of the selected portion to be examined (for example, an oral region, an ear region, and an eye region) among the head from the magnetic resonance signal received by the local coil 140.

The control device 150 stops a function of receiving the magnetic resonance signal by the local coil 140 while the RF coil 130 receives the magnetic resonance signal.

The control device 150 stops a function of receiving the magnetic resonance signal by the RF coil 130 while the local coil 140 receives the magnetic resonance signal.

The control device 150 is a console operated by an operator of the head-dedicated MRI device 100 according to the present disclosure, may be implemented as a workstation or a general computer, and may include an image display device, a keyboard, a mouse, and the like.

The housing 160 is manufactured in a hollow cylindrical shape such that only the head H and the portion of the shoulder S of the subject are accommodated in the inner hollow, and the main magnet 110, the gradient coil 120, and the RF coil 130 are installed in the housing 160.

For reference, in the head-dedicated MRI device 100 according to the present disclosure, since an image dedicated to the head H is acquired in a state in which only the head H and the portion of the shoulder S are conveniently moved into the housing 160 without the need for the subject to move the entire human body into the housing 160, the size of the device can be reduced, and the head-dedicated MRI device 100 can be installed and used in small hospitals.

Further, in the head-dedicated MRI device 100 according to the present disclosure, since only the head H and the portion of the shoulder S are moved into the housing 160, even a subject with claustrophobia can be comfortably photographed without fear for a closed space.

In particular, in the head-dedicated MRI 100 according to the present disclosure, since a body except for the head H may move during image capturing, fMRI obtained by measuring brain activity can be easily and variously acquired, and various functions of a brain can be viewed through the corresponding fMRI.

The installation frame 170 includes a ceiling portion 171 and a wall portion 172 to which the housing 160 is fixed.

For reference, it is preferable that, when the head-dedicated MRI device 100 according to the present disclosure is installed in a small hospital, a suitable installation space is secured, the installation frame 170 is disposed in the corresponding installation space, and as illustrated in FIGS. 1 to 7, the housing 160 is fixedly hung on the installation frame 170. Further, when it is difficult to secure the suitable installation space, the housing 160 may be fixedly hung on a ceiling or wall inside a building of the small hospital instead of the ceiling portion 171 or the wall portion 172 of the installation frame 170.

The vibration absorber 180 is interposed between an upper surface portion 161 of the housing 160 and the ceiling portion 171 of the installation frame 170, between a side wall portion of 162 the housing 160 and the wall portion 172 of the installation frame 170, or between a bottom surface of the housing 160 and a floor in which the installation frame 170 is installed, and connects the housing 160 and the installation frame 170.

For reference, FIGS. 1 to 7 illustrate an embodiment in which the vibration absorber 180 having a spring shape is interposed between the upper surface portion 161 of the housing 160 and the ceiling portion 171 of the installation frame 170 and between the side wall portion 162 of the housing 160 and the wall portion 172 of the installation frame 170.

While the head-dedicated MRI device 100 according to the present disclosure is operated to acquire an image, the vibration absorber 180 absorbs vibrations caused by the Lorentz force generated by the magnetic field of the main magnet 110 and a current applied to the gradient coil 120.

For reference, as illustrated in FIGS. 1 to 7, in a structure in which the housing 160 is fixedly hung on the installation frame 170, while an image is acquired, the vibrations caused by the Lorentz force generated by the magnetic field of the main magnet 110 and the current applied to the gradient coil 120 is generated, and due to these vibrations, noise is generated or image artifacts appear while an image is acquired.

When the vibration absorber 180 absorbs the vibrations, the noise generated by the corresponding vibrations or the image artifacts generated when the image is acquired can be removed.

In FIGS. 1 to 4, an embodiment in which a buffer spring is used as the vibration absorber 180 is described, but any structure and shape may be used as the vibration absorber 180 in addition to the buffer spring as long as the structure and shape can absorb vibrations in a state in which the housing 160 and the installation frame 170 are connected to each other.

The subject chair 190 includes a seat 191 on which hips and thighs of the subject are seated, armrests 192 installed on left and right sides of the seat 191, legrests 193 installed below the seat 191, a backrest 194 installed above the seat 191, and a headrest 195 installed to extend upward from the backrest 194.

The subject chair 190 may have any shapes as long as the shapes maintain a seated state of the subject such that only the head H and the portion of the shoulder S of the subject are accommodated in the inner hollow of the housing 160.

It is preferable that the subject chair 190 be manufactured such that the subject may freely move the head H and the portion of the shoulder S in a vertical direction, a front-rear direction, and a left-right direction in the inner hollow of the housing 160, it is preferable that the heights of the seat 191 and the headrest 195 be adjusted according to a physical condition of the subject, and it is preferable that inclination angles of the legrests 193 and the backrest 194 be adjusted.

The head-dedicated MRI device 100 according to the present disclosure operates as follows.

In a preparation process prior to start of the acquisition of the image, while seating on the subject chair 190, the subject freely moves the head H and the portion of the shoulder S in the vertical direction, the left-right direction, and the front-rear direction, and places the head H and the portion of the shoulder S thereof in the inner hollow of the housing, preferably, in the inner hollow of the main magnet 110.

In this state, the control device 150 is operated by the operator of the head-dedicated MRI device 100 according to the present disclosure, to start an image acquisition operation.

For example, when the fMRI obtained by measuring brain activity of the subject is acquired, when the control device 150 controls the pulse sequence applied to the gradient coil 120 and the RF coil 130, the RF coil 130 applies the RF electromagnetic waves causing the magnetic resonance phenomenon to the head H of the subject, blocks the RF electromagnetic waves, and then receives the magnetic resonance signal for acquiring the image of the entire head of the subject.

Accordingly, the control device 150 acquires an image of the entire head for brain diagnosis from the magnetic resonance signal received from the RF coil 130 and displays the image on the image display device.

Unlike this, for example, as illustrated in FIG. 5, when an image for dental diagnosis of the subject is acquired in a state in which the subject bites the mouthpiece-type oral coil 140 in a mouth to acquire the image for dental diagnosis, when the control device 150 controls the pulse sequence applied to the gradient coil 120 and the RF coil 130, the RF coil 130 applies, to the head H of the subject, the RF electromagnetic waves that cause the magnetic resonance phenomenon and blocks the RF electromagnetic waves.

Next, the control device 150 stops operation of a magnetic resonance signal reception function of the RF coil 130, and as described above, the mouthpiece-type oral coil 140 that the subject is biting in the mouth receives the magnetic resonance signal to acquire an image of an oral region corresponding to a portion to be examined selected from the head H of the subject.

Accordingly, the control device 150 acquires an image of the oral region for dental diagnosis from the magnetic resonance signal received from the mouthpiece-type oral coil 140 and displays the image on the image display device.

Unlike this, for example, as illustrated in FIG. 6, when an image for otologic diagnosis of the subject is acquired in a state in which a headphone-type ear coil 140 is fixed to a portion around an ear to acquire the image for otologic diagnosis, when the control device 150 controls the pulse sequence applied to the gradient coil 120 and the RF coil 130, the RF coil 130 applies, to the head H of the subject, the RF electromagnetic waves that cause the magnetic resonance phenomenon and blocks the RF electromagnetic waves.

Next, the control device 150 stops the operation of the magnetic resonance signal reception function of the RF coil 130, and as described above, the headphone-type ear coil 140 fixed to a portion around the ear of the subject receives the magnetic resonance signal to acquire an image of an ear region corresponding to a portion to be examined selected from the head H of the subject.

Accordingly, the control device 150 acquires an image of the ear region for otologic diagnosis from the magnetic resonance signal received from the headphone-type ear coil 140 and displays the image on the image display device.

Unlike this, for example, as illustrated in FIG. 7, when an image for ophthalmic diagnosis of the subject is acquired in a state in which an eyeglass-type eye coil 140 is fixed to a portion around an eye to acquire the image for ophthalmic diagnosis, when the control device 150 controls the pulse sequence applied to the gradient coil 120 and the RF coil 130, the RF coil 130 applies, to the head H of the subject, the RF electromagnetic waves that cause the magnetic resonance phenomenon and blocks the RF electromagnetic waves.

Next, the control device 150 stops the operation of the magnetic resonance signal reception function of the RF coil 130, and as described above, the eyeglass-type eye coil 140 fixed to a portion around the ear of the subject receives the magnetic resonance signal to acquires an image of an eye region corresponding to a portion to be examined selected from the head H of the subject.

Accordingly, the control device 150 acquires an image of the eye region for ophthalmic diagnosis from the magnetic resonance signal received from the eyeglass-type eye coil 140 and displays the image on the image display device.

According to the present disclosure, since a subject moves only a head and a portion of a shoulder into a housing without moving the entire human body into the housing and a head-dedicated image is acquired in this state, the size of a device can be reduced, and the device can be installed in a small hospital and used.

According to the present disclosure, since only the head and the portion of the shoulder move into the housing, an image of even a subject with claustrophobia can be comfortably captured without fear for a closed space.

According to the present disclosure, since the human body except for the head may move while the image is captured, fMRI obtained by measuring brain activity can be easily and variously acquired, and various functions of a brain can be shown through the corresponding fMRI.

According to the present disclosure, since a local coil manufactured in the form of being inserted into or worn in a human body of the subject is utilized, an image of a selected portion to be examined (for example, an oral region, an ear region, and an eye region) among the head can be acquired with a high signal-to-noise ratio (SNR).

According to the present disclosure, since vibrations caused by the Lorentz force generated while the image is acquired are absorbed by a vibration absorber installed around the housing, noise and image artifacts caused by the vibrations can be removed.

What is claimed is:

1. A head-dedicated magnetic resonance imaging (MRI) device comprising:
   a main magnet (110) is manufactured in a hollow cylindrical body such that only a head (H) and a portion of a shoulder(S) of a subject are accommodated in an inner hollow and applies electromagnetic waves to the head (H) of the subject, positioned in the inner hollow;
   a gradient coil (120) that is manufactured in a hollow cylindrical body installed in close contact with an inner diameter part of the main magnet (110) and applies a gradient magnetic field that temporarily changes a magnetic field intensity of the main magnet (110) according to the position of a portion to be examined, to encode information on the position of a portion to be examined of the head (H) of the subject located in the inner hollow;
   a radio frequency (RF) coil (130) that is manufactured in a hollow cylindrical body installed in close contact with the inner diameter part of the gradient coil (120), applies RF electromagnetic waves causing a magnetic resonance phenomenon inside the head (H) of the subject positioned in the inner hollow, blocks the RF electromagnetic waves, and then receives a magnetic resonance signal for acquiring an image of the entire head (H) of the subject;
   a local coil (140) that is manufactured in the form of being inserted into or worn in a human body of the subject, and after the RF coil (130) applies the RF electromagnetic waves causing the magnetic resonance phenomenon into the head (H) of the subject, and blocks the RF electromagnetic waves, receives the magnetic resonance signal for acquiring an image of a selected portion to be examined of the head (H) of the subject;
   a control device (150) that controls a pulse sequence applied to the gradient coil (120) and the RF coil (130) to determine application or blocking timing of the gradient magnetic field or application or blocking timing of the RF electromagnetic waves to be required for acquiring an image of the entire head of the subject or the selected portion to be examined among the head of the subject, acquires an image of the entire head for brain diagnosis from the magnetic resonance signal received by the RF coil (130), and acquires an image of the selected portion to be examined among the head from the magnetic resonance signal received by the local coil (140);

a housing (160) which is manufactured in a hollow cylindrical shape such that only the head (H) and the portion of the shoulder(S) of the subject are accommodated in the inner hollow and in which the main magnet (110), the gradient coil (120), and the RF coil (130) are installed;

an installation frame (170) that includes a ceiling portion (171) and a wall portion (172) to which the housing (160) is fixed; and a vibration absorber (180) that is interposed between an upper surface portion (161) of the housing (160) and the ceiling portion (171) of the installation frame (170), between a side wall portion (162) of the housing (160) and the wall portion (172) of the installation frame (170), or between a bottom surface of the housing (160) and a floor in which the installation frame (170) is installed, connects the housing (160) and the installation frame (170), and absorbs vibrations caused by the Lorentz force generated by the magnetic field of the main magnet (110) and a current applied to the gradient coil (120) while an image is acquired.

2. The head-dedicated MRI device of claim 1, wherein the main magnet (110), the gradient coil (120), and the RF coil (130) are installed in the housing (160) in a vertically upright state such that only the head (H) and the portion of the shoulder(S) of the subject are accommodated in the inner hollow.

3. The head-dedicated MRI device of claim 1, wherein the control device (150) stops a function of receiving the magnetic resonance signal by the local coil (140) while the RF coil (130) receives the magnetic resonance signal, and stops a function of receiving the magnetic resonance signal by the RF coil (130) while the local coil (140) receives the magnetic resonance signal.

4. The head-dedicated MRI device of claim 1, wherein the local coil (140) is any one of a mouthpiece-type oral coil inserted into a mouth to acquire an image for dental diagnosis of the subject, a headphone-type ear coil fixed to a portion around an ear to acquire an image for otologic diagnosis of the subject, and an eyeglass-type eye coil fixed to a portion around an eye to acquire an image for ophthalmic diagnosis of the subject.

5. The head-dedicated MRI device of claim 1, wherein the vibration absorber (180) absorbs vibrations caused by the Lorentz force generated by the magnetic field of the main magnet (110) and the current applied to the gradient coil (120) while an image is acquired in a state in which the housing (160) is hung on the installation frame (170).

* * * * *